United States Patent [19]

Welsh

[11] Patent Number: 5,811,627
[45] Date of Patent: *Sep. 22, 1998

[54] ALKYLATION REACTIONS

[76] Inventor: Stanley M. Welsh, 2813 E. Fox Chase Cir., Doylestown, Pa. 18901

[ * ] Notice: The term of this patent shall not extend beyond the expiration date of Pat. No. 5,557,028.

[21] Appl. No.: 713,747

[22] Filed: Sep. 13, 1996

Related U.S. Application Data

[63] Continuation-in-part of Ser. No. 14,409, Mar. 29, 1996.
[51] Int. Cl.$^6$ ............................... C07C 2/58; C07C 2/56
[52] U.S. Cl. .................. 585/732; 585/709; 585/722; 585/723; 585/724; 585/730; 585/731
[58] Field of Search ..................... 585/709, 722, 585/723, 724, 730, 731, 732

[56] References Cited

U.S. PATENT DOCUMENTS 5,557,028  9/1996  Welsh ........................... 585/724

*Primary Examiner*—Glenn Caldarola
*Assistant Examiner*—In Suk Bullock
*Attorney, Agent, or Firm*—Stanley M. Welsh

[57] ABSTRACT

Improved acid catalyzed alkylation reactions occur for the addition of a hydrocarbyl reactant to an alkene, by the optimized addition of an oxidizing agent, such as a peroxide, molecular oxygen, ozone, peracid, and one or more of the peroxide, molecular oxygen, ozone, or peracid mixed with at least one material selected from the group consisting of the hydrocarbyl reactant, and the alkene. The hydrocarbyl reactant contains at least one tertiary carbon atom attached to hydrogen, such as isobutane. The alkene is preferably an alkene of at least 2 carbon atoms. Suitable peroxides are found in the group consisting of: tert-butyl peroxyneopentanoate $((CH_3)_3C-O-OCO-C(CH_3)_3)$; acetyl peroxide $(CH_3CO-O-OCOCH_3)$; di-tert-butyl peroxide $((CH_3)_3C-O-O-C(CH_3)_3)$; hydrogen peroxide $(H_2O_2)$ and peracids of carboxylic acid having up to 10 carbon atoms, and a general chemical formula $C_nH_{2n}O_3$, where n has values in the range 2-10. Examples of peracids having the general chemical formula are: perisopentanoic acid: $(CH_3)_3CCO-O_2H$ corresponding to $C_5H_{10}O_3$); peracetic acid: $CH_3CO-O_2H$ corresponding to $C_2H_4O_3$. Kolbe-like reactions are also used to directly or indirectly to catalyze the addition to an alkene of hydrocarbyl materials containing a tertiary carbon bonded to hydrogen through a free radical on the tertiary carbon of isobutane or of a "branched tertiary alkyl carbon" hydrocarbyl reactant. Preferably, the carboxylate group is attached to either the tertiary carbon of isobutane or a "branched tertiary alkyl carbon".

28 Claims, 2 Drawing Sheets

ALKYLATION REACTIONS

CROSS-REFERENCE TO RELATED APPLICATIONS

Some of the information and inventions disclosed in this Specification was previously disclosed in U.S. application Ser. No. 08/414709 filed Mar. 31, 1995 and issued as U.S. Pat. No. 5,557,028 (Sep. 17, 1996).

This application is a continuation-in-part application of a provisional application U.S. Ser. No. 60/014,409 (Attorney Docket No. SMW1PA) Filed Mar. 29, 1996.

BACKGROUND OF THE INVENTION

1. Field of the Invention

This invention relates to the preparation of gasoline blending additives used to increase a transportation fuel's octane. More specifically, this invention relates to the use of strong acids, like sulfuric or hydrofluoric acids, or electrochemical reactions, such as Kolbe-like reactions, to catalyze the addition of tertiary carbon atoms such as found in t-butane to an alkene such as found in 2-butene, ethylene, or propylene.

2. Description of the Prior Art

In the presence of a very strong acid, such as substantially pure sulfuric or hydrofluoric acid, the addition of alkenes to alkanes containing a tertiary carbon atom bound to hydrogen is reported to involve in one of its propagation reactions a hydride ion transfer from the tertiary carbon to an alkane-alkene intermediate. An example of these propagation reactions is:

$(CH_3)_3C(+) + CH_2=CHCH_2CH_3 \longrightarrow$
(t-carbonium ion)

$(CH_3)_3CCH_2C(+)HCH_2CH_3$
(alkane-alkene intermediate)

$(CH_3)_3CCH_2C(+)HCH_2CH_3 + (CH_3)_3CH \longrightarrow$ $(CH_3)_3CCH_2CH_2CH_2CH_3 + (CH_3)_3C(+)$
(alkylation product)

The production of a new tertiary carbonium ion that adds to another alkene allegedly drives the reaction forward as alkylation products such as 2,2-dimethyl hexane and acid catalyzed rearrangements thereof are separated from the reaction medium. To avoid side reactions, such as alkenes reacting with the alkane-alkene intermediate or themselves, excess alkane over alkene is used, often on the order of 20:1 weight percent alkane:alkene. The reaction temperature is usually kept low in the range of 10°–20°C.

Examples of such literature references are briefly cited below.

Kirk-Othmer Encyclopedia of Chemical Technology (Fourth Edition, Vol. 2, page 87) refers to three studies of strong acid catalysis of tertiary carbon addition to an alkene. These studies were: L. Schmerling, *Journal of the American Chemical Society*, Vol. 68, 275 (1946); F. G. Ciapetta, *Industrial Engineering Chemistry*, Vol. 37, 1210 (1945); and J. E. Hoffman & A. J. Schriescheim, *Journal of the American Chemical Society*, Vol. 84, 953–961 (1962).

In the *Journal of the American Chemical Society*, Vol. 73, 5741 (1951) in an article entitled, "The Behavior of Isobutane in Concentrated Sulfuric Acid", J. W. Otvos, D. P. Stevenson, C. D. Wagner, and O. Beeck reported that L. Schmerling's interpretation of the alkylation of alkenes by isobutane was essentially correct. They found: 1. no skeletal isomerization of either n-butane or isobutane; 2. there was no hydrogen exchange between molecules of n-butane (intermolecular) or between primary and secondary carbon atoms of a single n-butane (intramolecularly); 3. the tertiary hydrogen of t-butane does not exchange with acid protons of sulfuric acid, but the primary hydrogens do; 4. the tertiary hydrogens can be made to exchange by the addition of 0.1% of either isobutylene or 2-butene; 5. the apparent exchange rate between tertiary deuterated $C^{13}$ labeled and $C^{12}$ unlabeled isobutane revealed the rate of loss of tertiary D from the labeled isobutane matched the rate of increase in the amount of D in the unlabeled isobutane.

These results provided the basis for proposing the following reaction scheme:

$(CH_3)_3C^{12}(+)+(CH_3)_3C^{13}D \longleftrightarrow (CH_3)_3C^{12}D+(CH_3)_3C^{13}(+)$ $(CH_3)_3C^{13}(+)+(CH_3)_3C^{12}H \longleftrightarrow (CH_3)_3C^{13}H+(CH_3)_3C^{12}(+)$

These experimental observations and interpretations have lead to the universally accepted conclusion that scrambling of tertiary deuterium atoms of isobutane (also known as 2-methylpropane, tert-butane, isobutane, i- or t-butane) was due to a hydride ion transfer of a tertiary hydrogen of isobutane to a secondary or tertiary carbonium ion produced indirectly by protonation of an alkene or from an addition product intermediate that results from isobutylene adding to itself due to an acid catalysis.

In summary, the sulfuric acid catalyzed addition of isobutane to an olefin, which occurs at below 50° C., such as propylene or butene, was believed to require a hydride ion transfer of the tertiary hydrogen of isobutane to an alkane-alkene intermediate containing a carbonium ion to produce another tertiary carbonium ion that would propagate the reaction by adding to another olefin.

Provided that the alkane, such as t-butane, is in large enough excess over the alkene, the formation of polymers or polyadducts can be suppressed and minimized.

In the *Journal of the American Chemical Society*, vol. 71, 2015–2019 (1949) in an article entitled, "Peroxide-induced Condensation of Saturated Hydrocarbons with Polychloroethylenes" Louis Schmerling and James P. West reported the following reactions:

1)

2)

3)

4)

where: X=H or Cl and Y=Cl; R'=t-butyl group; R=a variety of alkanes including t-butane.

The following reaction numbered 6) was not reported presumably because it did not occur in detectable amounts:

The major products appeared to result from reactions shown in equations 4) and 5). Equation 4) is a disproportionation reaction and Equation 5) is a simple biradical coupling reaction. If the reactions of equations 4) and 5) predominate over those of 3) and 6) under all conditions, then the usefulness of a free radical induced addition of an alkane to an alkene would not be particularly useful for commercial production of octane additives.

Louis Schmerling disclosed alkylation reactions of saturated hydrocarbons with olefins or alkenes: in the presence of molecular oxygen and hydrogen chloride at a temperature in the range 100°–400° C. and a pressure of 1 to 100 atmospheres in U.S. Pat. No. 3,855,325 (Dec. 17, 1974); and in the presence of peroxy compounds and hydrogen chloride at temperatures in the range 50°–300° C. and pressures in the range 1 to 100 atmospheres or even higher in U.S. Pat. No. 3,773,843 (Nov. 20, 1973). Temperatures in excess of 50° C. were required to generate within a reasonable amount of time a reasonable amount of free radicals either due to oxidation with molecular oxygen or due to thermally decomposed free radical initiating peroxy compounds. Taught is the need to have hydrogen chloride present to moderate the free radical reactions initiated either by molecular oxygen or peroxy compounds to avoid making high molecular weight species. Not taught is that at low temperatures either substantially pure sulfuric or hydrofluoric acid, promote at an organic/inorganic interface formation of a free radical on a tertiary carbon atom of a hydrocarbyl material containing a tertiary carbon bonded to a hydrogen suitable for alkylation with an alkene to form octane blending components (1:1 adducts) without the need for hydrogen chloride to be present to moderate the free radical reactions. Also not appreciated is the fact that even though very strong acids destroy free radicals, the presence of an organic phase provides a medium that hydrocarbyl materials with a tertiary carbon free radical can migrate into or be produced within at under 50° C., preferably under 40° C., and still more preferably under 30° C. in the presence of sulfuric acid or hydrofluoric acid. For optimal results the acids are substantially pure. Presence of hydrochloric acid inhibits the migration or production of hydrocarbyl free radicals in the organic phase.

The Kolbe Reaction is a well known electrochemical reaction that involves an oxidation at an anode of the carboxylate ion of an organic acid to produce either a free radical or a carbonium ion depending upon the electrode used and the voltage applied. These reactions are as follows:

7) $RCH_2CO_2^- - \Theta^- \rightarrow RCH_2CO_2 \cdot$

8) $RCH_2CO_2 \cdot \rightarrow RCH_2 \cdot + CO_2$

9) $RCH_2 \cdot - \Theta^- \rightarrow RCH_2(+)$

10) $RCH_2 \cdot \rightarrow RCH_2-CH_2R$ where R is either a hydrogen or a saturated or unsaturated hydrocarbyl material, that can include, esters, amines, amides, ketones, etc. When a carbon electrode is used instead of platinum, there is a tendency to remove two electrons at the anode, thereby generating a carbonium ion shown in equation 9. When precious metal anodes such as platinum, tin, gold, silver, or palladium, are used, the more usual course of the reaction is to generate the free radical shown in equation 8. This radical can and often does couple with itself in a bi-radical coupling reaction in accordance with equation 10.

The literature has reported that free radicals produced at the anode can react with highly active alkenes and even catalyze formation of polymers such as polystyrene from styrene monomers. However, none of these efforts to use radicals generated electrochemically have provided a commercially viable alternative to presently practiced acid catalyzed alkylation of i-butane with alkenes to make octane blending components for transportation fuels, such as discussed above.

In *Topics in Current Chemistry*, vol. 152, pages 92–151, the addition of Kolbe Radicals to double bonds was discussed. Reference was made to the work of Louis Schmerling and James P. West reported in the *Journal of the American Chemical Society*, vol. 71, 2015–2019 (1949). The conclusions reached are provided on page 142 of volume 71. Among these conclusions were: (a) due to the high concentration of radicals in the reaction layer in front of the electrode, termination and not propagation predominates even in the presence of alkenes; (b) in the presence of high current, dimers are favored; (c) elevated pressures favor Kolbe Coupling; (c) high temperatures favor disproportionation; (d) high current favored formation of additive monomers and low current favored additive dimers; (e) in the presence of reactive olefins such as butadiene, isoprene, or styrene good yields of adduct were observed; (f) foreign cations ranging from most to least effective in producing lower yields are $Fe^{+2}<Co^{+2}<Ca^{+2}<Mn^{+2}<Pb^{+2}$ and alkali metals, alkaline rare earth metals, alkylammonium ions, zinc, or nickel ions do not seem to affect or influence Kolbe Reactions.

In reaching this invention, the inventor began with the conviction that the mechanism proposed for the acid catalyzed alkylation reaction of isobutane and an alkene could not be right. The reasoning was as follows. It is very unlikely that simple thermal energy at temperatures under 50° C. will be sufficient to polarize the C-H bond in tertiary butane merely by the approach of a secondary or even a tertiary carbonium ion so that the transition state:

$(CH_3)_3C(+)-H(-)-(+)CHRR'$;

where R and R' are any hydrocarbyl group such as found in a typical alkylation adduct, is reached. As the transition state of highest energy is approached, the hydrogen in the C-H bond allegedly becomes more and more negative. Since a hydrogen atom in a chemical bond with carbon is simply a very small proton nucleus surrounded by electrons that are primarily under the influence of carbon molecular orbitals, a more accurate picture of the hydrogen to carbon bond is a hydrogen nucleus imbedded in the electron cloud that surrounds the carbon atom. Although Schmerling in U.S. Pat. Nos. 3,855,325 and 3,773,843 considered the use of free radicals in the presence of hydrochloric acid to initiate alkylation reactions with saturated hydrocarbons and alkenes, the possibility that similar reactions could be occurring at much lower temperatures and in the absence of hydrochloric acid when concentrate sulfuric or hydrofluoric acid was being used was discounted, probably because: (1) strong acids are known to destroy free radicals, consequently it would be expected that sulfuric or hydrofluoric acid would inhibit rather than facilitate free radical alkylation reactions; and (2) Louis Schmerling taught and advocated that in the case of alkylations catalyzed by concentrated sulfuric acid, a hydride ion transfer rather than a hydrogen atom (free radical) transfer was required. The uniqueness of the concentrated sulfuric acid and hydrofluoric acid catalyzed alkylations arises from the presence of low temperatures and an organic/inorganic interface.

Surprisingly, Kolbe-like reactions when properly run prove to be commercially equivalent in inducing alkylation reactions in much the same manner as strong acid catalysis, wherein hydrocarbyl free radicals on tertiary carbons either migrate into or are formed within a hydrocarbyl reaction phase.

Utility and Objects of the Invention

In light of the importance of producing blending components to increase the octane of transportation fuels such as diesel and gasoline, this invention discloses in part and in some of its embodiments ways to vary process variables for a conventional acid catalyzed alkylation of a hydrocarbyl specie containing at least one tertiary carbon to an alkene that improves yields and process performance, such as reducing the amount of an organic sludge and other environmentally undesirable side reactions that would otherwise be produced.

In light of the environmentally undesirable side reaction products that are often produced in for example a sulfuric acid catalyzed alkylation reaction of i-butane with an alkene; and in light of the hazards from using sulfuric or hydrofluoric acid as a catalyst; and in light of the difficulty in finding stable superacid catalysts which could replace sulfuric or hydrofluoric acids; this invention provides in part an alternative approach through electrochemistry or oxidizing agents promoted by strong acids to reach very useful products while avoiding environmentally undesirable side reaction products, and use of hazardous materials like sulfuric and hydrofluoric acids.

SUMMARY OF THE INVENTION

General Statement of the Invention

Improved ways to run a conventional strong acid catalyzed alkylation reaction in surprising and unexpected ways become evident to one, once one realizes that there is a free radical mechanism involved. Such an alternative mechanism must account for the products produced and explain how a tertiary hydrogen of a hydrocarbyl specie like isobutane is transferred to a reaction product intermediate formed during the acid catalyzed addition of the hydrocarbyl specie to an olefin.

The actual mechanism involves a transfer of a hydrogen atom (a free radical) rather than a transfer of a hydride ion. Additional evidence justifying this alternative mechanism is available. However, this information has been overlooked until now for almost 50 years! The evidence is as follows.

A small amount of oxygen is almost inevitably entrained in any alkene. This fact is clear from the anti-Markovnikov addition of hydrobromic acid to 1-pentene. HBr adds to 1-pentene to yield 1-bromopentane and 2-bromopentane in a ratio of Markovnikov (2-bromopentane) to anti-Markovnikov (1-bromopentane) that varied depending upon the amount of exposure to air. These results were explained in terms of a free radical catalyzed addition of HBr and an acid catalyzed addition of HBr to the 1-pentene. In a free radical catalyzed reaction, a bromide radical adds to the primary carbon, because a secondary carbon radical is more stable than a primary carbon radical. In an acid catalyzed reaction, a proton adds to the primary carbon of 1-pentene, because a secondary carbonium ion is more stable than a primary carbonium ion. Hence, it is clear that either a radical or a positive charge is most favored on a tertiary carbon atom, followed by a secondary carbon atom, followed by the least favored, a primary carbon atom. The free radical addition of HBr is suppressed by the presence of hydroquinone or other free radical scavengers.

In the mechanism proposed to explain how and why this invention works, a free radical is generated in the presence of oxygen and a very strong acid in an organic phase. The very strong acid, which includes sulfuric, hydrofluoric, or a superacid catalyst such as discussed by Tanabe et al. and Olah et al. in their respective books cited hereinafter, activates molecular oxygen or other oxidizing agents such a peroxides, to promote removal of a hydrogen atom (neutral free radical) from a hydrocarbyl material containing a tertiary hydrogen; thereby producing an alkyl free radical at low temperatures. A low temperature is important to lessen disproportionation reactions which tend to be promoted by steric hinderance in tertiary alkyl radicals, such as two t-butyl radicals. Further, control of the amount of any oxidizing agent presence in the organic phase is important to maximizing yields, since any free radical generated will itself be suject to oxidation by that oxidizing agent. Once the free radical is in the organic phase, it will survive in spite of the well known property that strong acids destroy free radicals. In fact, by introducing oxidizing agents, such as ozone or peroxides, "near" the interface between organic and inorganic phases, initially within the organic phase, presence of the strong acid will facilitate their decomposition at low temperatures, such as below 50° C., preferably below 40° C., and still more preferably below 30° C., so as to encourage formation of alkyl free radicals within the organic phase, as such oxidizing agents migrate to the interface. This then provides a consistent alternative explanation of what caused the rapid transfer of hydrogen between labelled tertiary butanes when isobutylene was added. The isobutylene introduced a small amount of oxygen which turned the tertiary carbon into a free radical. Transfer of hydrogen atoms, neutral free radicals, explains the results. The energy required for such an exchange is considerably lower than that which would be required for a hydride ion transfer under similar circumstances of temperature and pressure.

This then explains how simply bubbling a radical generating agent like oxygen with or without an alkene sufficiently near an interphase between a strongly acidic phase and an organic phase consisting of hydrocarbyl species that contain a tertiary carbon bonded to hydrogen will cause free radicals to be generated in the organic phase. The alkene is preferably diluted with the hydrocarbyl species to reduce acid catalyzed coupling of alkenes. The organic phase preferably includes, but is not required to, a hydrocarbyl material which can dissolve the hydrocarbyl specie and alkene and which is substantially insoluble in the strongly acidic phase.

The reactions proceed in the following way:

Initiation Reactions:

In Acid Catalyzed System:

$(CH_3)_3CH$(oxidizing agent, $O_2$ and a strong acid at the interface)→$(CH_3)_3C\cdot$ In Kolbe Catalyzed System
Direct Method:

$$(CH_3)_3COO^- - \Theta^- \rightarrow (CH_3)_3C\cdot + CO_2$$

Indirect Method:

$$RCOO\text{--}\Theta^- \rightarrow R + CO_2$$

$$R + (CH_3)_3CH \rightarrow RH + (CH_3)_3C\cdot$$

Where in the indirect method R is preferably a "branched tertiary alkyl carbon" group (as defined hereinafter) or a halogenated hydrocarbyl such as: $CX_nH_{3-n}$ wherein X is a halogen and n takes on any integer value from 0 to 3; or $R'CX_nH_{2-n}$, wherein R' is a hydrocarbyl and n' takes on an integer value from 1 to 2. Collectively, these carboxylic acids will be referred to as stericly hindered carboxylic acids.

Propagation Reactions:

$$(CH_3)_3C\cdot + CH_2\!\!=\!\!CH\text{--}CH_2CH_3 \rightarrow (CH_3)_3\text{--}CH_2\text{--}C(\cdot)H\text{--}CH_2CH_3$$

$$(CH_3)_3\text{--}CH_2\text{--}C(\cdot)H\text{--}CH_2CH_3 + (CH_3)_3CH \rightarrow (CH_3)_3\text{--}CH_2\text{--}CH_2\text{--}CH_2CH_3 + (CH_3)_3C\cdot$$

The chemical significance or consequence of an abstraction of any one of the 9 possible primary hydrogens of t-butane instead of the single tertiary hydrogen initially or otherwise will quickly be lost as a result of equilibrating exchanges among t-butanes, because the stability of a tertiary carbon radical is so much greater than that of a primary carbon radical. The indirect Kolbe method permits the use of acetic acid as an example of a specie which gives rise to a methyl radical which in turn abstracts a hydrogen from the isobutane. The methyl radical after abstraction of a hydrogen atom becomes a gas. Accordingly, any hydrocarbyl carboxylic acid of from 2 to 4 carbon atoms has the useful advantage of becoming a gas upon abstraction of a hydrogen atom from t-butane. For examples, methane is produced with use of acetic acid, ethane, with propanoic acid, and propane, with butanoic acid. Such gases are readily separated.

Once the hydrocarbyl specie that contains a tertiary carbon bonded to a hydrogen atom, such as tertiary butane, becomes a free radical at or very near the interface where the organic phase and the acid phase meet, or is formed as a result of a Kolbe-like reaction, rapid migration of that free radical-like species into or throughout the organic phase will occur. The migration of the free radical-like species merely requires a series of hydrogen atom jumps between t-butane molecules. The migration is very rapid, much like the apparent migration of a solvated proton through an aqueous phase. The destruction of radical species including any radical generating agent such as the following oxidizing agents: ozone or a peroxide that one might expect from the presence of a strong acid is at least in part overcome due to the rapid migration of the free radical of the hydrocarbyl specie away from the interface and into the organic hydrocarbyl reaction phase. Also undesirable side reaction due to radical fragments, such as may be produced by the interaction of ozone or oxygen with radical intermediates, are suppressed. Finally, using branched tertiary alkyl carbons and halogenated hydrocarbyls inhibits the free radicals produced in Kolbe-like reactions from coupling and running the reactions at low temperatures lessens disproportionation reactions.

Protonation of alkenes introduced into the organic hydrocarbyl reaction phase is preferably avoided in order to minimize side reactions such as an acid catalyzed addition of one alkene with another or formation of an organic sludge in general. One way to minimize such side reactions is to add alkenes only at a distance away from the acid/organic interface, so that diffusion or other forms of migration to the interface by an alkene will not occur significantly in contrast to migration of reactive hydrocarbyl intermediates that have a tertiary carbon free radical. In addition, it would be preferable to add fresh hydrocarbyl species between the point of addition of additional alkenes to the organic phase and the acid/organic interface, so that there is a net flow of material away from the interface into other portions of the hydrocarbyl reaction phase, which further lessens the tendency of an alkene to migrate to the interface and become protonated.

Since contact between alkenes and the protonating tendency of the acid phase is minimized, a much cleaner reaction process design is possible without the requirement for high energy mixing of the acid and organic phases to form emulsions or dispersions.

For purposes of this specification and claims, several terms are defined in the immediately following paragraphs.

The term "superacid catalyst" identifies materials such as discussed by Tanabe et al. and Olah et al. in their respective books referred to hereinafter. Generally, these are solid catalysts characterized in that they are suitable to replace (partially or totally) sulfuric acid or hydrofluoric acid as catalytic agents to promote alkylation reactions between alkanes and alkenes. An example of such an alkylation reaction is the addition of isobutane to propylene or butene.

The term "hydrocarbyl" when used to identify a portion of a molecule (a "hydrocarbyl" or a "hydrocarbyl group"), material, specie, medium, intermediate, blending component, or phase shall mean a portion of a molecule, material, specie, medium, intermediate, blending component, or phase that consists essentially of carbon and hydrogen atoms with no more than 5% by weight of other atoms such as oxygen, halide, nitrogen, or sulfur, preferably less than 1% and still more preferably less than 0.1% by weight. "Halide" includes one or more atoms of fluorine, chlorine, bromine, or iodine. Preferably, there will be less than 1% by weight, and ideally substantially none of such other atoms present in the hydrocarbyl. Preferably, the hydrocarbyl contains less than 10 carbon atoms.

The term "branched tertiary alkyl carbon" means any material that results when one or more hydrogens attached to any carbon that is directly attached to a tertiary carbon are replaced with a hydrocarbyl group. A "branched tertiary alkyl carbon group" is that portion of a molecule that results when the tertiary hydrogen formerly attached to the tertiary carbon is removed. Examples of hydrocarbyl materials containing a "branched tertiary alkyl carbon" are 1,1-dimethyl butane and 2-methyl butane. A "tertiary carboxylic acid of a branched tertiary alkyl carbon group" means any organic acid that results from attaching a carboxylate group to the tertiary carbon in place of the tertiary hydrogen and similarly, a "tertiary carboxylic acid of a hydrocarbyl material containing a tertiary carbon attached to a tertiary hydrogen" means any organic acid that results from replacing the tertiary hydrogen with a carboxylate group. Examples of a tertiary carboxylic acid of a hydrocarbyl material containing a tertiary carbon or tertiary carboxylic acid of a branched tertiary alkyl carbon group are 2,2-dimethyl propanoic acid and 2,2-dimethyl butanoic acid.

The term "Kolbe-like reactions" means all electrochemical reaction processes wherein a free radical is produced at an anode, such as when a carbon attached to a carboxylate yields carbon dioxide and a free radical on the carbon. The term "hydrocarbyl acid precursor" means that carboxylate ion which when oxidized at an anode yields a "hydrocarbyl radical" which results from removing a carboxylate group and leaving in its place a free radical on the carbon previously attached to said carboxylate group.

The term "near" an interface between phases is a relative term which will depend upon the amount of mixing that is occurring at the interface and the stability of the radical generating agent to strong acid. For example, if the addition of molecular oxygen at the interface causes a great deal of mixing between the two, then the distance from the interface preferably will be larger to take into account a greater tendency of the acid phase to migrate into the hydrocarbyl organic phase. However, if the radical generating agent is very unstable, then addition near the interface will preferably be into the organic phase, or preferably with a diluent when added into the acid phase. Any hydrocarbyl free radical generated preferably is given an opportunity to migrate into the organic phase without being destroyed by the presence of any strong acid. Other materials such as an alkene, having from 2 to 10 carbon atoms, can be added "near" the interface to encourage reaction between the alkene and a hydrocarbyl free radical, having from 4 to 10 carbon atoms, wherein the radical is on a tertiary carbon.

The term "encouraging" in the sense of facilitating the reaction of a free radical addition to an alkene means adopting one or more of the following strategies: 1) controlling amount present of an oxidizing agent such as oxygen: (a) within the reaction zone containing all of the reactants, such as the alkanes, alkenes, and any acid; or (b) within any of the feed streams such as i-butane, alkene, or mixture thereof just prior to addition to a reaction zone containing a strong acid such as sulfuric or hydrofluoric or a superacid catalyst, and maintaining reactants at a temperature, wherein each are individually optimized to achieve at least 80% of the maximum yield otherwise achievable by varying the amount of the oxidizing agent present, while keeping all other process variables substantially constant, and preferably at least 90% of said maximum yield. Examples of such other process variables include maintaining a sufficient excess of alkane over alkene in the hydrocarbyl reaction phase so as to reduce and preferably eliminate unwanted side reactions such as two or more alkenes coupling to form species having more than 8–15 carbon atoms; adding alkane or recycling material (as for example a reaction phase stream) "near" the interface so as to promote a net flow of reactants away from the interface and thereby inhibit diffusion of alkenes to the interface where they might become protonated; separating products from the hydrocarbyl reaction phase to form a reaction phase stream and a product stream and recycling back at least a portion of the reaction phase stream into the hydrocarbyl reaction phase "near" the interface. The precise location of the recycle stream is not critical, but it can be used to reduce side reactions and promote free radicals, as for example when used as a diluent for the radical generating agent. The amount of oxygen present will generally be at least about 0.01% by weight, more preferably at least 0.05% by weight, and still more preferably at least 0.5% by weight, as based upon the weight of alkene present, and generally in the range of 0.05 to 2% by weight of the weight of alkene present.

A strategy especially suitable for superacid catalysts involves avoiding (totally or partially) contact between the superacid catalyst and any alkene reactants, while promoting the formation of hydrocarbyl activated intermediates, such as hydrocarbyl free radicals, which activated intermediates, preferably, in the substantial absence of any superacid catalyst, are brought into contact with reactant alkenes. Deactivation or stability problems associated with most superacid catalyst arises from polymerization of alkenes catalyzed by the presence of a strong acid. By avoiding or significantly minimizing contact between alkene reactants and the superacid catalyst, one can decrease rates of catalytic deactivation significantly and reverse such deactivation as occurs much more easily.

The term "sufficient excess" in general will depend upon the particular reactant and reaction conditions. A "sufficient excess" of alkane over alkene will inhibit side reactions to less than 5% by weight, and preferably less than 1% by weight, and still more preferably less than 0.1% by weight and ideally less than 0.01% by weight as based upon product yields of octane blending products.

The term "substantially optimizing a reaction process or its yields by control of a selected process variable such as amount of an oxidizing agent or free radical generating agent that produces directly or indirectly a tertiary carbon radical from t-butane" means throughout this specification and claims to control said selected process variable to a value wherein carrying out the process keeping all other process variables substantially constant, results in a yield of useful products equal to at least 80% and still more preferably at least 90% of the maximum achievable yield obtainable by optimizing said selected process variable, while keeping all other variables substantially constant.

Addition of molecular oxygen so as to pass from the strongly acidic phase into the hydrocarbyl reaction phase is preferably carried out so as to maximize the amount of tertiary carbon atom free radicals produced in the hydrocarbyl reaction phase. It is to be noted that it should be possible to produce some 2,2,3,3-tetramethylbutane, a specie which provides the largest increase in octane of all known hydrocarbyl blending components; provided reaction temperature is kept low and disproportionation reactions minimized. Temperature control is necessary to optimize yield of 2,2,3,3-tetramethylbutane and lessen formation of disproportionation products like isobutane and isobutylene.

Unreacted molecular oxygen should be removed from the system and preferably recycled. A build up of molecular oxygen in the acid phase is undesirable, because it often leads to the formation of water. Any significant amounts of water present will cause sulfuric acid or hydrofluoric acid to become intolerably corrosive with much more severe wear on production equipment than would otherwise occur simply from the use of pure sulfuric acid or hydrofluoric acid. To maintain the acid phase in a substantially anhydrous condition, the addition of anhydrous $SO_3$ or fuming sulfuric acid to the sulfuric acid from time to time is recommended. Fuming sulfuric acid contains $SO_3$ which reacts with water to form sulfuric acid. Also during regeneration by methods well known in the art of either sulfuric or hydrofluoric acid to remove organic components, water removal by methods also well known in the art is recommended.

Separation of such molecular oxygen can be carried out through a sudden drop in pressure of the hydrocarbyl reaction phase or decantation in a gas liquid separation vessel or both carried out alternately or simultaneously. Separation of products from the hydrocarbyl reaction phase can be carried out by distillation and other methods well known in the relevant art.

Consistent with promoting a t-butyl radical addition to an alkene, by means of a Kolbe-like reaction, the electrochemically generated radical is transferred from the immediate area of an anode into a large excess of t-butane—like material, e.g. a non-polar and substantially organic only hydrocarbyl phase, to suppress disproportionation or biradical coupling reactions. The shifting of hydrogen atoms among the various tertiary carbon-containing materials suppresses the formation of dimers, encourages free radical propagation reactions, and allows one to control both temperature and concentrations to optimize and promote alkylation reactions. Preferably the organic acid used in the Kolbe-like reaction is a tertiary carboxylic acid of a "branched tertiary alkyl carbon".

Flow through electrochemical cells that simultaneous use a non-aqueous organic electrolyte and an aqueous based electrolyte have been disclosed in the literature. The cells are arranged so as to maintaining substantially complete separation of the non-aqueous organic electrolyte from that of an aqueous based electrolyte. A particularly useful example of such a cell suitable for this invention is one that is used to produce adiponitrile ($NC-(CH_2)_4-CN$) from acetyinitrile ($CH_2=CH-CN$) through reduction at a cathode. A schematic diagram of such a cell is in *Techniques of Electroorganic Synthesis,* Edited by Norman L. Weinber, Published by John Wiley & Sons (1974) vol. V, parts 1 & 2.

The invention of this specification is the first time that flow through cells have been found to be useful in the commercial production of gasoline octane blending components. High concentrations of free radicals in the vicinity of the anode is overcome, provided a sufficiently high flow rate is utilized along with electrodes that do not adsorb free radicals too strongly.

BRIEF DESCRIPTION OF THE FIGURES

Inventive and novel modifications in FIGS. 1 and 2 are identified by numbers in excess of 1000 and 2000, respectively.

DETAILED DESCRIPTION OF THE INVENTION AND PREFERRED EMBODIMENTS

In an otherwise conventional strong acid catalyzed reaction of isobutane and an alkene, one controls the amount of molecular oxygen or other agent that leads to the formation of tertiary carbon free radicals. Several places are available for such control. To understand where they are, schematic overviews of conventional sulfuric and hydrofluoric acid catalyzed alkylation units are modified respectively in FIGS. 1 and 2 in accordance with this invention.

Figure 1:
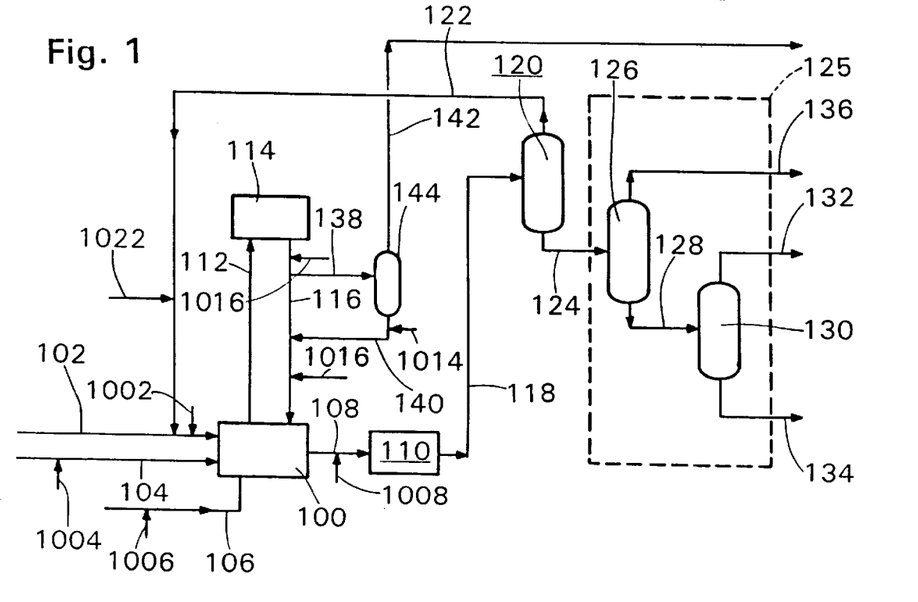
FIG. 1 is a schematic diagram of a typical sulfuric acid alkylation unit modified in accordance with this invention.

Modern Petroleum Technology 4th Edition, edited by G. D. Hobson in collaboration with W. Pohl, and published by Applied Science Publishers LTD discusses a sulfuric acid alkylation on pages 348 to 350. FIG. 1 without inventive features is an example the sulfuric acid alkylation unit disclosed. The process involves:

contacting in a first reaction zone (identified as reactor 100), an isobutane introduced through conduit 102 and an alkene or olefin feed introduced through conduit 104 with sulfuric acid initially introduced through conduit 106;

separating and then transferring through conduit 108 a predominantly organic stream from reactor 100 to acid removal vessel 110;

transferring via conduit 112 a predominantly acid stream to vessel 114;

treating said predominantly acid stream in vessel 114 to refrigerate and by an internal recycle consisting of vessel 144 and conduits 138, 140, and exit conduit 142 for propane both: to remove propane from the system; and to recycle the remainder back to reactor 100;

replacing with fresh acid through conduit 106 at least a portion of spent sulfuric acid removed from reactor 100 and not recycled following treatment in refrigeration vessel 114 and propane removal vessel 144;

treating in an acid removal vessel 110 the predominantly organic stream to substantially remove all acidic components, and then transferring the resulting organic stream through conduit 118 to deisobutanizer 120 which produces:

1) an isobutane recycle stream transferred through conduit 122; and 2) a debutanizer stream transferred through conduit 124 to debutanizer system 125 (shown within a dashed rectangular box) comprising first separation vessel or debutanizer 126 and a rerun or second separation vessel 130;

treating the debutanizer stream in debutanizer vessel 126 to separate:

1) from a bottom layer therein, a debutanizer product which is transferred through conduit 128 to second separation vessel 130 for final separation into two or more alkylate streams (the acid catalyzed adducts of isobutane and alkene feeds) depending upon their molecular weight which are removed from debutanizer system 125 through conduits 132 and 134; and 2) from overheads thereof, an n-butane stream which is removed through conduit 136.

The feed streams to reactor 100 are: fresh isobutane which enters through conduit 102; recycled isobutane which enters through conduit 122; fresh acid which enters through conduit 106; recycled acid which first exits from reactor 100 through conduit 112 after which it is partially treated following transfer via conduit 138 from recycle conduit 116 to vessel 144 to remove propane through conduit 142 before return from vessel 144 to conduit 116 via conduit 140. The streams from the reactor are: a predominantly organic stream which exits reactor 100 through conduit 108 and which contains entrained acidic components; and a spent acid stream separated by decantation which exits through conduit 112 and returns in part through conduit 116 while also in part being discarded as propane through conduit 142 and waste acid through a conduit not shown. The temperature of the reactor is kept at a temperature in the range 4° to 13° C. for optimal results. The alkylation reaction is quite exothermic and the temperature is preferably kept below 20° C. for optimal results. The more isobutane as measured in liquid hourly space velocity the generally higher is the octane of the alkylate product streams separated.

The predominantly organic stream is often separated from most of the acidic components by a simple process of settling followed by decantation to form a predominantly organic stream which is then treated in treating vessel or zone 110 to remove entrained acidic materials. Caustic and water washing, or bauxite or hot water washing are all possible ways of treating the predominantly organic stream to remove acidic components and produce a debutanizer feed comprising substantially only organic materials which are removed from treating vessel 110 through conduit 118.

The modifications of FIG. 1 which allows a conventional acid catalyzed alkylation process to be carried out in accordance with the invention of this specification are shown as additional conduits labelled with numbers in excess of 1000. These conduits permit the addition of an oxidizing agent such as molecular oxygen in controlled amounts. Ideally, the amount of oxygen for example in the predominantly organic stream exiting through conduit 108 is monitored to provide a gauge as to how much molecular oxygen to add in order to appropriately optimize process conditions. Conduits for addition of an oxidizing agent such as molecular oxygen to materials contained within particular conduits found in a conventional sulfuric acid catalyzed alkylation unit are respectively: conduit 1002 for conduit 102; 1004 for 104; 1006 for 106; 1008 for 108; 1016 for 116 before or after internal recycle for conduit 138; 1014 for 140; and 1022 for 122.

An alternative reactor design to that given above is disclosed in *Petroleum Refining Technology and Economics Second Edition,* edited by James H. Gary and Glenn E. Handwerk, and published by Marcel Dekker, Inc of New York and Basel on pages 169 and 170. The acid contacting vessel provides for incremental addition of the olefin to a series of zones. The acid contacting is carried out in as many as five separate zones, with effluent from each prior zone being transferred to an immediately subsequent zone. Since the olefin is introduced in incremental amounts, the process could be modified in accordance with one embodiment of this invention to control and therefore adjust the molecular oxygen present in either the olefin to optimize the yields that are achieved or incrementally into each zone either as part of the stream transferred between zones or as a separate addition.

Figure 2:
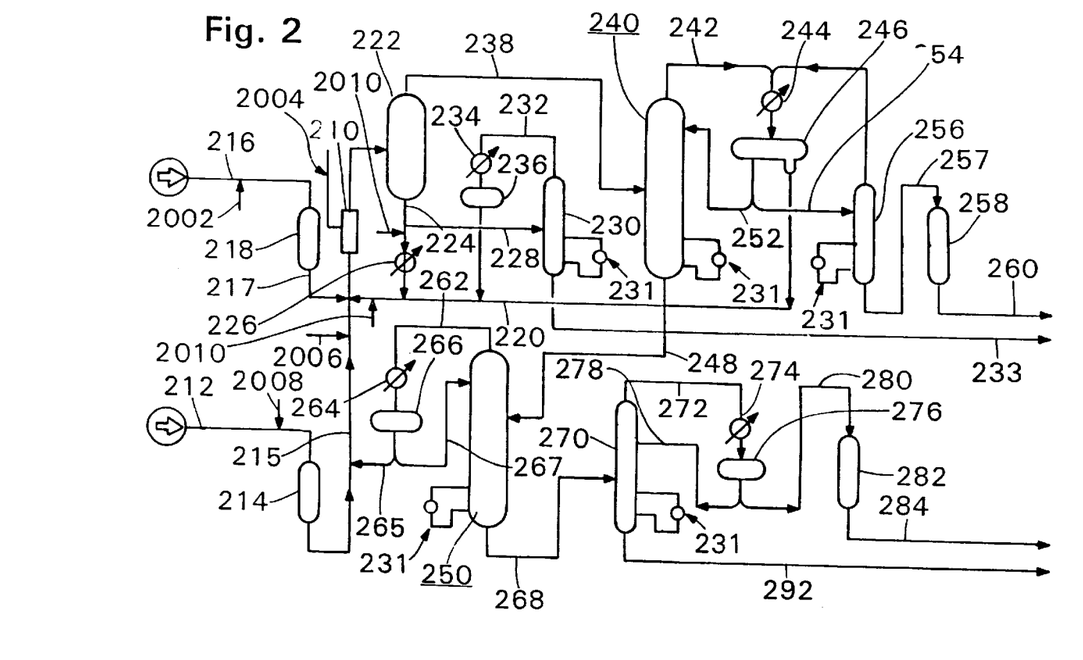
FIG. 2 is a schematic diagram of a typical HF alkylation unit modified in accordance with this invention.

*Petroleum Refining Technology and Economics Second Edition,* edited by James H. Gary and Glenn E. Handwerk, and published by Marcel Dekker, Inc of New York and Basel on page 165 discloses a hydrofluoric acid process which is shown in FIG. 2, except that conduits numbered in excess of 2000 disclose the process modified in accordance with the invention of this specification. The HF catalyzed alkylation consists of:

mixing in flow reactor 210: 1) a dehydrated isobutane stream produced by passing isobutane through conduit 212, isobutane feed drier vessel 214, and conduit 215; 2) a dehydrated alkene or olefin stream produced by passing an alkene or olefin feed through conduit 216, alkene feed drier vessel 218, and conduit 217; and 3) a predominantly hydrofluoric acid recycle stream carried by conduit 220; to form a reaction product stream (sufficient temperature and pressure being maintained in flow reactor 210 and acid settler vessel 222 to maintain HF in a liquid phase);

separating the reaction product stream in settler vessel 222 into:

1) a predominantly acid stream, which being more dense forms a bottom layer that is transferred from settler vessel 222 via conduit 224: a) in part to acid cooler 226 to remove at least a portion of any heat of reaction and maintain the acid hydrocarbon mixture at no more than 30° C., and generally in the range 70°–80° F. (21°–27° C.) for ultimate return as a cooled acid stream via conduit 220 to flow reactor 210; and b) in part as a slip-stream via conduit 228 to an acid rerun vessel 230 from which: i) an overhead product of substantially pure hydrofluoric acid is recycled through conduit 232 and cooler 234 to storage vessel 236 before return via conduit 220 to flow reactor 210; and ii) a bottom layer of waste acid is removed from the system via conduit 233;

2) a predominantly organic layer, which being less dense is a top layer within settler vessel 222, that is transferred through conduit 238 to depropanizer 240;

distilling from the top of depropanizer 240 propane and HF via conduit 242 and heat exchanger or cooler 244 into a depropane accumulator 246; and decanting a primarily isobutane stream from a bottom layer formed within depropanizer vessel 240 through conduit 248 to debutanizer vessel 250;

decanting from depropane accumulator 246:

1) at least a portion of a top layer within depropane accumulator 246 as a recycle stream via conduit 252 to depropanizer 240 and transferring via conduit 254 a second portion to acid stripper 256 and then via conduit 257 to a propane caustic treater 258 and final removal from the system via conduit 260 as propane; and 2) a bottom layer consisting essentially of pure HF from depropanizer accumulator 246 via conduit 220 as an HF recycle to flow reactor 210;

fractionating in deisobutanizer vessel 250, to form:

1) a recycle of substantially pure isobutane through conduit 262 and heat exchanger 264 into deisobutanizer accumulator vessel 266, from which a first portion of isobutane is recycled back to flow reactor 210 via conduit 265 and 215 and a second portion of isobutane is returned via conduit 267 to deisobutanizer vessel 250; and 2) a debutanizer stream transferred via conduit 268 to debutanizer vessel 270;

fractionating in debutanizer vessel 270 to form:

1) an overhead stream consisting of n-butane with some acidic components that is transferred via conduit 272 and heat exchanger 274 into debutanizer accumulator 276 from which a recycle stream is transferred via conduit 278 back to debutanizer vessel 270 and a stream for treatment to remove acidic components is transferred via conduit 280 to butane caustic treater vessel 282 and ultimate removal from the system via conduit 284 as n-butane; and 2) a bottoms stream of product alkylate that is transferred out of the system via conduit 292.

Vessels: 230; 240; 250; 256; and 270; are disclosed to have internal recycle systems 231 to help equilibrate the vapors contain within them, and to ensure a liquid condensate at the bottom of them. These generalized internal recycles 231 have a condenser or heat exchanger to cool materials being recycled internally.

Through one or more conduits numbered in excess of 2000, an oxidizing agent such as molecular oxygen is added. The preferred location for such addition is the HF recycle either before or after acid cooler 226 to conduit 224 or 220, respectively via conduits 2010. Alternatively, molecular oxygen may be added: to the alkylene feed conduit 216 via conduit 2002; directly to flow reactor conduit 210 via 2004; or to conduit 215 via conduit 2006; or to the isobutane feed conduit 212 via conduit 2008

As between the alkylene and isobutane feed, addition to the isobutane feed is preferred.

In general, in an acid catalyzed alkylation, where an alkane is added to the acid prior to the addition of any alkene, it is preferable in accordance with this invention to add controlled amounts of an oxidizing agent such as molecular oxygen to the acid or the alkane or both in a mixture thereof, prior to introducing the alkene and producing an emulsion of acid, alkane, and alkene. However, more typically, the alkane and alkene are mixed together with an excess of alkane to alkene and then together are made into an emulsion or dispersion with the acid. In general, regardless of location for addition of alkane and/or alkene, the process conditions that control product yield and product distribution are: weight hourly space velocity which relates contact time between an organic phase and an acid phase in units of weight of organic phase to volume of acid phase per hour; ratio of alkane to alkene which is preferably at least 1.5 moles of alkane to each mole of alkene, preferably at least 5 moles of alkane for each mole of alkene and still more preferably at least 10 moles of alkane for each mole of alkene and generally the ratio in moles of alkane to alkene is in the range of about 1.5:1 to 20:1; temperature which is preferably kept under 40° C. is generally in the range of about 0° to 30° C.; pressure at a value sufficient to maintain volatile components of alkanes and alkenes in solution and as liquids; and now recognized for the first time as explained in this specification, the amount of oxidizing agent, such as for example, molecular oxygen present in any of the feed streams, including that of the acid. The oxidizing agent that results in a free radical forming directly or indirectly on isobutane can be added as a separate stream to the acid phase.

In summary, the well known variables which control course of a strong acid catalyzed addition of a hydrocarbyl containing a tertiary carbon atom bound to hydrogen to an alkene are: weight hourly space velocity as measured by the volume of acid contacted by organic components per volume of such organic components per hour; temperature; pressure; concentrations of alkane, alkene, and acid components; ratio of acid to organic components; ratio of alkanes to alkenes; mixing efficiencies; separation and recycle rates and efficiencies; and acid purity and strength. The commonly used acid catalysts include sulfuric acid, hydrofluoric acid, and superacid catalysts. Examples of relevant superacid catalysts can be found in *Superacids* by Olah, et al. published by John Wiley & Sons and in *New Solid Acids and Bases Their Catalytic Properties* by Kozo Tanabe, et al. Elsevier (1989).

Still another way to run the reaction in accordance with this invention is to expose the alkene to oxygen prior to mixing with the alkane. Then instead of forming an acid emulsion or dispersion, which is still an option, simply pass the mixture as preferably finely dispersed bubbles or droplets through at least a portion of the acid phase of for example either sulfuric or hydrofluoric acid. Additional alkenes are preferably added with or without additional alkanes to the organic phase, which is separate and distinct from the acid phase. A key to reaction performance of this embodiment is to control the amount of molecular oxygen dissolved in the alkene and temperature of reactants, preferably below 20° C., and more preferably below 10° C. Preferably the values for temperature and amount of oxygen are those which optimize yields, all other factors remaining substantially constant, to at least 80% and still more preferably to at least 90% of maximum yield otherwise achievable.

In *Laboratory Techniques in Electroanalytical Chemistry,* edited by Peter T. Kissinger & William R. Heineman, published by Marcel Dekker, Inc. N.Y. there is a report on a flow cell suitable for this invention which is shown schematicly in FIG. 3 and in detail in FIG. 4.

Figure 3:
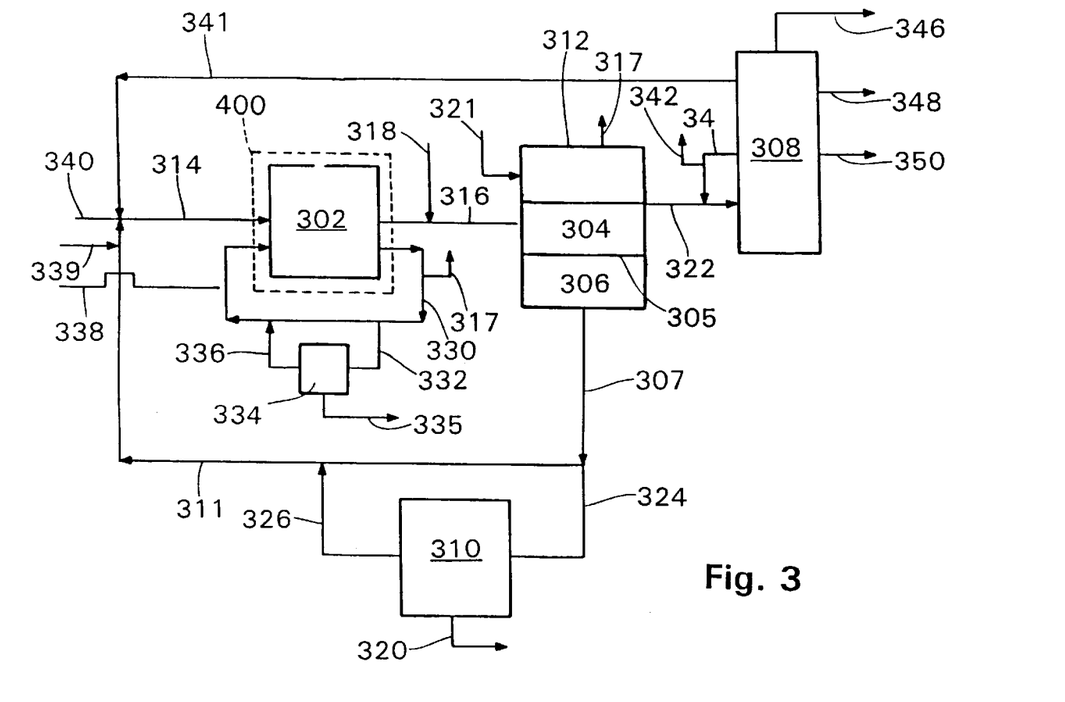
FIG. 3 is schematic diagram of an electrochemical alkylation unit that uses an electrochemical cell shown in more detail in FIG. 4.
Figure 4:
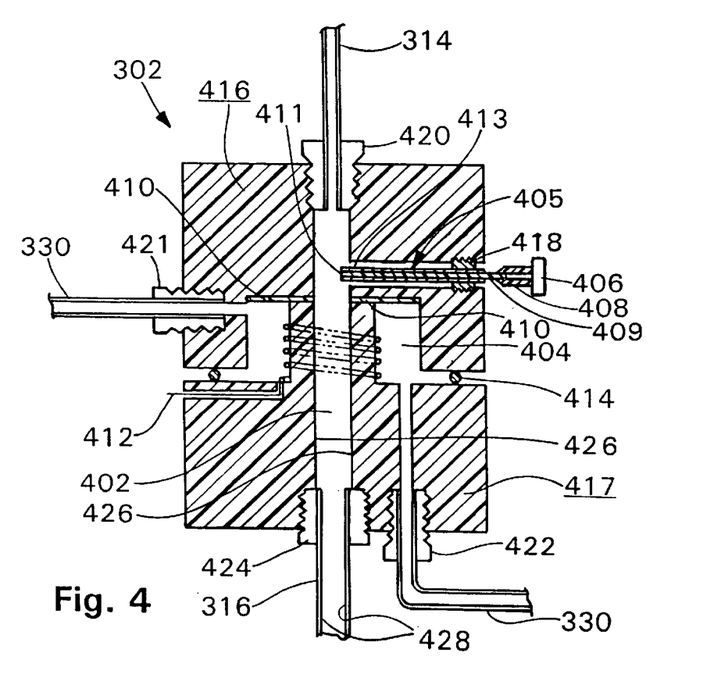
FIG. 4 is a cross-sectional side elevation view of an electrochemical cell suitable for producing alkyl radicals that catalyze addition of t-butanes to alkenes.

With reference to FIG. 3 when numbers in the 300's are used and FIG. 4 when numbers in the 400's are used, an embodiment of this invention is disclosed, wherein an electrochemical cell 302 is used to generate a catalyzing amount of i-butyl or t-butyl free radicals either directly or indirectly in a hydrocarbyl reaction medium comprising isobutane and an alkene. Not shown specifically is the fact that to inhibit decomposition of free radicals at metallic surfaces, especially those containing iron, at least a portion of the walls or interior surfaces 426 of anodic pathway 402 of cell 302, static mixers or other mixing elements such as stirrers (preferably present but not expressly shown) contained in conduit 316, through which anodic electrolyte and hydrocarbyl reactants added through conduit 318 are transferred to settler vessel 312, and at least a portion of the interior walls or surfaces of settler vessel 312 itself, are all made of or coated with a material which is non-reactive with hydrocarbyl or alkyl free radicals. An example of such non-reactive material is a perfluorinated hydrocarbyl material, such as Teflon.

The input streams to cell 302 are as follows. I-butane and alkenes as part of fresh feed enters the anodic pathway 402 of cell 302 through conduits 314 and 340 or as part of a recycle stream through conduits 314 and 341. Note that conduits 340 and 341 may be more than one conduit. Carboxylate feed enters through conduit 339 directly or indirectly (as shown) into conduit 314. An anodic electrolyte feed is also introduced into the anodic pathway 402 of cell 302 through recycle conduit 311 and conduit 314. Fresh cathodic electrolyte feed can be introduced as needed through conduit 338 into recycle conduit 330.

The Kolbe-like reaction at the anode 405 of cell 302 gives rise to a free radical such as described earlier. In preferred embodiments, the carboxylate feed is a "tertiary carboxylic acid of a hydrocarbyl material containing a tertiary carbon attached to a tertiary hydrogen" group (as defined earlier) or a halogenated hydrocarbyl such as: $CX_nH_{3-n}$ wherein X is a halogen and n takes on any integer value from 0 to 3; or $R'CX_nH_{2-n}$, wherein R' is a hydrocarbyl and n' takes on an integer value from 1 to 2. These hindered carboxylic acids tend to be less reactive to biradical coupling and consequently remain active within conduit 316 and often reach settler vessel 312 through conduit 316. Conduit 316 preferably contains static mixing elements or other mixing elements such as at least one stirrer to improve mixing of all reactants. Accordingly, conduit 316 functions at least in part like a flow reactor.

The key point is to remove the free radicals formed in the neighborhood of the anode and dilute them with i-butane reactants. Into flow reactor 316, alkene reactants are added through conduit 318.

In settler vessel 312, anodic electrolyte feed, comprising for example, methanol and KOH, forms bottom layer 306 separated by interface 305 from top layer 304 comprising hydrocarbyl reactants, products, and intermediates. At least a portion of bottom layer 306 is recycled through conduits 307 and 311 and returned to cell 302 along with fresh carboxylate feed introduced through conduit 339. Optionally, a portion of the anodic electrolyte feed is withdrawn as a slip stream from bypass conduit 311 through conduit 324 into a purification vessel 310. From purification vessel waste products and side reaction products are removed through conduit 320 as required. The remainder of the slip stream is returned to bypass conduit 311 for return to cell 302. Top layer 304 comprising free radical adduct products and unreacted hydrocarbyl reactants such as alkenes and isobutanes are transferred through conduit 322 to fractionation columns schematicly represented as a single vessel 308. However, as would be obvious to a person of average skill in the art, single vessel 308 is in practice several vessels such as are used to separate butanes from isobutanes and other hydrocarbyl materials depending upon their molecular weight and volatility.

The following discussion refers to vessel 308. The various streams separated in schematic vessel 308 are: alkylate products through conduit 346; a small amount of oxygen containing materials such as alcohols through conduit 348; n-butanes through conduit 350; and isobutanes and alkenes through recycle conduit 341 which is schematicly shown as a single conduit, but in practice usually comprises more than one conduit: one for isobutane and another for alkene reactants. Alkenes are preferably added to conduit 316 substantially exclusively through conduit 318. Carbon dioxide formed due to a Kolbe-like reaction process are removed through conduit 317. Internal recycle 344 of fractionation column 308 is preferably cooled and optionally has a conduit 342 for removal of low molecular weight hydrocarbons.

Cathodic electrolyte feed is circulated through recycle conduit 330. Recycle conduit 330, optionally has a purification vessel 334 from which contaminated cathodic electrolyte waste products are removed through conduit 335. Also Hydrogen produced at the cathode are removed from cathodic electrolyte recycle conduit 330 through conduit 317.

In general, any anodic electrolyte feed that has only very limited solubility for the hydrocarbyl reactants of isobutane and alkene are preferred.

With reference to FIG. 4, a more detailed view of cell 302 is shown. Cell 302 consists of two segments 416 and 417 which form two passageways referred to as anodic pathway 402 and cathodic pathway 404, when a fluid tight seal is formed between segments 416 and 417 by means of a combination of o-ring 414 and cation exchange membrane 410 comprising a resilient seal forming material. Optionally, an o-ring (not shown) like that one corresponding to o-ring 414 can be used in conjunction with cation exchange membrane 410 to form a fluid tight seal between segments 416 and 417. Conduits 314, 316, and 330 of FIG. 4 are the same as those shown in FIG. 3. The conduits have been cut off to show only the portion of cell 302 outlined with dotted line 400 in FIG. 3. Conduit 314 forms a fluid tight seal with cell body of first segment 416 of cell 302 by means of a threaded coupling 420 and conduit 316 similarly makes a fluid tight seal with cell body of second segment 417 by means of a threaded coupling 424. The entering portion of conduit 330 makes a fluid tight seal with cell body of first segment 416 by means of threaded seal coupling 421 and another fluid tight seal between exit portion of conduit 330 and cell body of second segment 417 by means of threaded coupling 422. Rotating anode 405 has a conductive core 409 surrounded by a nonconductive ceramic 413. At one end of rotating anode 405 is a polished surface 411 in the shape of a disk, which is disposed within anodic pathway 402. At the other end of rotating electrode 405 is an exposed section of conductive core 409. A fluid seal is formed between bearing insert 418 and outer ceramic surface 413. O-rings not shown can be used to provide both a fluid tight seal and one which permits rapid rotation of spinning electrode 405. The exposed section of conductive core 409 is suited for being held by clamp 408 which transmits torque produced by motor 406. Voltage is applied through clamp 408 and conductive core 409. Anodic feed enters through conduit 314 into anodic pathway 402 of cell 302 and passes rotating anode 405. In general, the ratio of volume of anodic pathway 402 to volume of rotating electrode is in the range of about 2:1 to 20:1. Rotating or spinning electrodes are available from: Princeton Applied Research, N.J. and Bio Analytical Systems, Indiana, such as a sealed 4 mm (millimeter) ID and 12 mm OD teflon shroud upper with a spin limit depending upon the onset of turbulence around 5,000 rpm. The combination of linear or plug flow through conduit 314 and stirring caused by rotating electrode 405 in anodic pathway 402 ensures that free radicals produced at electrode surface 411 do not remain concentrated near other radicals or the electrode. Free radicals produced by electrode 405 are carried from anodic pathway 402 via conduit 316 which optionally has static mixing elements (not shown) into settler vessel 312. Disposed within cathodic pathway 404 is a working electrode 412 which contacts cathodic electrolyte feed passing through conduit 330. As current flows through both 412 and rotating anode core 409 in response to an applied voltage across cathode and anode, cation exchange membrane 410 allows ionic transfer of hydrogen ions between anode and cathode sections to maintain electrolyte balance and current.

The materials used for the electrochemical cell are reported in Analytical Chemistry, vol. 51 (7) page 800 (June 1979) to consist of: two 2" diameter Plexiglass blocks, flow rate: 10 ml./minute, with a working electrode consisting of a copper wire, cation exchange membrane washers, 10 mils thick 0.219 inches in diameter, 1.068 inches O.D. Nafion XR-170, sold by E.l. du Pont de Nemours Company, Del. The reference electrode consisted of a 0.1M KCl saturated AgCl was flushed through the cavity at about 0.1 mL/minute through the cavity containing Ag-AgCl reference electrode. The reagents for the supporting electrolyte was 0.1M phosphate buffer (pH 7.4) with a 1:1 mixture $KH_2PO_4$ and $K_2HPO_4$. The dimensions for a full scale production cell will be considerably larger. Rotating electrode 405 spins for example in the case of a production cell in excess of 1,500 revolutions per minute. The maximum rate of speed appropriate will depend on the viscosity of the anodic electrolyte medium. The speed of rotation and flow through the cell are such as to remove radicals formed at or near surface 411 at a rate sufficient to substantially suppress termination reactions such as coupling reactions between free radicals and encourage propagation reactions such as reactions between free radicals and t-butane or alkenes.

The cell reaction conditions are in general: 1) smooth platinum anode and a platinum, steel or nickel cathode associated through a polyelectrolyte (to be discussed in more detail later in this specification); 2) a current density of 0.25 Amperes/centimeter$^2$ (cm$^2$); 3) slightly acidic or neutral electrolyte (to be discussed in more detail later in this specification); and 4) maintain temperature between 10° and 45° C.

Examples of suitable anode electrodes are: materials selected from the group consisting of Groups VII and IB of the Periodic Table of The Elements, Aluminum, Tin, Zinc, Lead, Titanium, Carbon as graphite or reticulated vitreous carbon (RVC) of an electrochemical cell.

Examples of suitable non-aqueous electrolyte media for Pt and Anodic voltage limits are:

| Solvent | Electrolyte | Cathodic Limit | Anodic Limit |
|---|---|---|---|
| acetonitrile | (n-but)$_4$N ClO$_4$ | −3.0 | 2.5 |
| acetonitrile | (Et)$_4$N BF$_4$ | −1.8 | 3.2 |
| pyridine | (Et)$_4$N ClO$_4$ | −2.2 | 3.3 |
| sulfolane | (Et)$_4$N ClO$_4$ | −2.2 | 3.0 |
| methanol | KOH | −1.0 | 0.6 |

For a review of non-aqueous solvent and suitable electrolytes, reference electrodes, useable potential ranges, and solvent purification techniques see C. K. Mann, *Electroanalytical Chemistry*, A. J. Bard, Editor, Vol. 3, page 57, Published by Marcel Dekker, New York (1969).

For purposes of this invention, the anodic reaction medium or solution: (a) is only partially soluble in the hydrocarbyl reaction medium in which free radical reaction of the indirectly or directly generated free radical of isobutane reacts with an alkene; and (b) separates rapidly and easily in a settling vessel for easy recycling to the anode. Foreign cations ranging from most to least effective in producing lower yields are $Fe^{+2}<Co^{+2}<Ca^{+2}<Mn^{+2}<Pb^{+2}$ and alkali metals, alkaline rare earth metals, alkylammonium ions, zinc, or nickel ions do not seem to affect or influence Kolbe Reactions can be added to the anodic reaction medium to moderate diradical coupling and formation of terpolymers, and other side reactions and increasing rate of separation in settler vessel 312.

Appropriate cells for producing hydrocarbyl free radicals in a hydrocarbyl medium such as described appropriate for phase two of this invention can be found in *Journal of the Electrochemical Society,* Vol. 130, 533–538 (1983) wherein use of Nafion membranes are discussed. Unlike the instant invention, the electrochemical reaction disclosed involved two molecules of acrylonitrile which are each reduced by transfer of an electron to each molecule at the cathode. Two negative free radicals of acrylonitrile join to form a doubly negative reaction intermediate which upon transfer of two protons from water yields adiponitrile. By contrast the organic electrochemical reaction of this invention takes place at the anode. Details as to the best procedure for carrying out a Kolbe-like reaction are disclosed in *Advances in Organic Chemistry: Methods and Results,* Published by Interscience Publishers, Vol. 1, beginning on page 5 (QD 251.A36).

For appropriate cell designs that utilize electrolytes in an organic or aqueous phase that flow passed relevant electrodes in conjunction with the use of polyelectrolytes such as Nafion, see *Techniques of Electroorganic Synthesis* (QD 61.T4) Edited by N. L. Weinberg, and published by John Wiley and Sons, volume V, parts 1 and 2. Cell designs appropriate for commercial applications are specifically discussed along with the parameters of aqueous and non-aqueous solvents suitable for particular current and voltage ranges.

Modifications

Specific compositions, methods, or embodiments discussed in this specification are intended to be only illustrative of the claimed invention. Variations of any of these that would be readily apparent to a person of skill in the art based upon the teachings of this specification and the knowledge and skill of a person of ordinary skill in the relevant art are intended to be within the scope of the disclosed invention.

For example, suitable radical generating agents, which are usually also oxidizing agents that can be usefully added or produced in-situ in carrying out this invention include the following: tert-butyl peroxyneopentanoate (($CH_3$)$_3$C—O—OCO—C($CH_3$)$_3$); acetyl peroxide ($CH_3$CO—O—O—CO$CH_3$); di-tert-butyl peroxide (($CH_3$)$_3$C—O—O—C($CH_3$)$_3$); hydrogen peroxide ($H_2O_2$) and peracids of carboxylic acid having up to 10 carbon atoms, and a general chemical formula $C_nH_{2n}O_3$, where n has integer values in the range 2–10. Examples of peracids having the general chemical formula are: perisopentanoic acid: ($CH_3$)$_3$CCO—O$_2$H corresponding to $C_5H_{10}O_3$); peracetic acid: $CH_3$CO—O$_2$H corresponding to $C_2H_4O_3$.

For still another example of a variation within the intended scope of this invention involves coating certain reaction walls of a typical strong acid catalyzed alkylation system so as to inhibit decomposition of hydrocarbyl free radicals recognized in this specification as potentially critical reaction intermediates. As was discussed with respect to Kolbe-like reactions which directly or indirectly induce the formation of a free radical on a tertiary carbon of a hydrocarbyl group, coating surfaces of walls, conduits, and means for mixing or stirring such as static mixers or stirrers likely to come into contact with free radical intermediates with a non-reactive material such as perfluorinated hydrocarbons like Teflon, facilitates the alkylation process by promoting propagation reactions over termination reactions.

Still another variation within the scope of this disclosure is the use of exchange rates of isobutyl hydrogens as a method for determining the effectiveness of a catalyst to promote addition of a hydrocarbyl material containing a tertiary hydrogen to an alkene. Clearly, the exchange rate must be faster or of the same order of magnitude as that promoted by the presence of substantially pure sulfuric acid to establish suitability of a catalyst for such addition reactions. Proton Nuclear Magnetic Resonance is particularly suited for detecting and measuring such hydrogen exchanges.

Reference to all or any portion of any document made any where in the specification is intended to result in all such documents, be they patents, or any other printed publications, including documents referenced in such documents, being expressly incorporated herein by reference in their entirety.

Each expressly identified numerical range within this specification is intended to incorporate by reference and therefore expressly include and provide express support as required by 35 U.S.C. 112 for each and every numerical member of each such range including each and every possible range within each such expressly identified numerical range. For example, a numerical range of 1 to 100, is intended to provide express support for any range within such numerical range, such as 3 to 28, or 72 to 94 etc. and also to provide express support for any specific numerical member of the range 1 to 100, such as 25, or 63 etc.

The invention which is claimed is:

1. A process for producing at least one hydrocarbyl blending component to improve gasoline octane comprising:

near an interface between two phases comprising a first phase and a second phase, generating a free radical on a tertiary carbon atom of a hydrocarbyl reactant containing said tertiary carbon atom; wherein said first phase and said second phases are characterized in that they are at a temperature under 50° C. and substantially insoluble in one another, wherein said first phase comprises a superacid catalyst; and wherein said second phase comprises a hydrocarbyl reaction medium comprising said hydrocarbyl reactant;

encouraging reaction of said free radical with an alkene within said second phase by controlling amount of an oxidizing agent to optimize yield of said at least one hydrocarbyl blending component.

2. The process of claim 1, wherein said oxidizing agent is at least one member selected from a group consisting of a peroxide, oxygen, and ozone in an amount controlled to optimize yield of said at least one hydrocarbyl blending component.

3. The process of claim 2, wherein said oxidizing agent is a peroxide.

4. The process of claim 2, wherein said oxidizing agent is oxygen.

5. The process of claim 2, wherein said oxidizing agent is ozone.

6. The process of claim 2, wherein said oxidizing agent is a combination of oxygen and ozone.

7. The process of claim 3, wherein said peroxide is selected from the group of peroxides consisting of: peracids having a general chemical formula: $C_nH_{2n}O_3$, where n=an integer of from 2–10; tert-butyl peroxyneopentanoate; acetyl peroxide; di-tertbutyl peroxide; and hydrogen peroxide.

8. The improved process of claim 2, wherein to optimize means to maintain that amount of said oxidizing agent which promotes a yield which is at least 80% of maximum reachable yield through control of said amount of said agent while all other factors are held substantially constant.

9. The improved process of claim 8, wherein said yield is at least 90% of said maximum reachable yield.

10. The process of claim 2, wherein said oxidizing agent is diluted with at least one material selected from the group consisting of said hydrocarbyl reactant, said hydrocarbyl reaction medium, said hydrocarbyl blending component, and said alkene.

11. In a process that uses a superacid catalyst to catalyze reaction between an alkene and a hydrocarbyl reactant containing a tertiary carbon bonded to hydrogen, the improvement which comprises producing a free radical on said tertiary carbon by contacting said hydrocarbyl reactant with an oxidizing agent which is activated by said acid and whose amount is controlled to substantially optimize said process.

12. The improved process of claim 11, wherein to substantially optimize said alkylation process, amount of said oxidizing agent is controlled so that said yield which is achieved is at least 80% of maximum reachable yield through optimal control of amount of said agent.

13. The improved process of claim 12, wherein said yield which is achieved is at least 90% of said maximum reachable yield.

14. The improved process of claim 11, wherein said oxidizing agent is at least one member selected from a group consisting of a peroxide, molecular oxygen, and ozone, and is mixed with at least one material selected from a group consisting of said hydrocarbyl reactant, said alkene, and said superacid catalyst prior to reaction between said hydrocarbyl reactant and said alkene.

15. The improved process of claim 14, wherein said oxidizing agent is a peroxide.

16. The improved process of claim 15, wherein said peroxide is selected from the group of peroxides consisting of: a peracid having a general chemical formula: $C_nH_{2n+1}CO-O_2H$, where n=an integer value of from 2–10; tert-butyl peroxyneopentanoate; acetyl peroxide; di-tert-butyl peroxide; and hydrogen peroxide.

17. The improved process of claim 14, wherein said oxidizing agent is a combination of molecular oxygen and ozone.

18. The improved process of claim 11, wherein said reaction involves a step of forming a mixture comprising a member selected from a group consisting of: said alkene; and said hydrocarbyl reactant; with said superacid catalyst; wherein said oxidizing agent is added to said mixture.

19. The improved process of claim 11, wherein said reaction involves a step of forming a mixture comprising said alkene, said hydrocarbyl reactant and a superacid catalyst, and wherein said oxidizing agent is added to said mixture.

20. The improved process of claim 19, wherein said agent is added to at least one of a material selected from the group consisting of said alkene and said acid prior to forming said mixture.

21. In a process for adding a hydrocarbyl specie to an alkene, wherein said hydrocarbyl specie contains at least one tertiary carbon atom bonded to hydrogen and wherein contact with a superacid catalyst is used to form gasoline blending components which improve octane, the improvement which comprises prior to contacting a feed comprising said hydrocarbyl specie and said alkene with said superacid, controlling amount of oxygen within said feed to substantially optimize yield for said gasoline blending component.

22. The improved process of claim 21, wherein to substantially optimize said yield, amount of said oxygen is controlled so that said yield for said gasoline blending component is at least 80% of maximum yield reachable for said gasoline blending component through optimal control of amount of said oxygen.

23. A process for catalyzing addition of a hydrocarbyl reactant to an alkene, wherein said hydrocarbyl reactant contains at least one tertiary carbon atom bonded to a tertiary hydrogen, said process comprising:

producing at an anode a hydrocarbyl radical by means of a Kolbe-like reaction involving its corresponding ionized hydrocarbyl acid precursor while dissolved or dispersed in an anodic reaction medium;

transferring said hydrocarbyl radical including at least a portion of said anodic reaction medium away from said anode and mixing at least a portion thereof with a hydrocarbyl reaction medium comprising isobutane and an alkene to form a reaction mixture;

separating from at least a portion of said reaction mixture a product stream of hydrocarbyl reaction products comprising molecules containing at least six carbon atoms and a first recycle stream comprising unreacted isobutane and alkene;

recycling at least a portion of said recycle stream into said hydrocarbyl reaction medium;

whereby a commercial process for making hydrocarbyl blending components suitable for gasoline is achieved without using strong acids, like sulfuric or hydrofluoric, or superacid catalysts.

24. The process of claim 23, additionally comprising separating from an at least a portion of said reaction mixture a second recycle stream comprising said anodic reaction medium, and recycling at least a portion thereof back to said anode and said anodic reaction medium.

25. The process of claim 24, wherein said anodic reaction medium is selected from a group of solvents consisting of: acetonitrile; pyridine; sulfolane; and methanol.

26. The process of claim 25, wherein said hydrocarbyl acid precursor, when not ionized, is selected from a group of organic acids consisting of: acetic acid; halogenated acetic acid; and a carboxylic acid group attached directly to a tertiary carbon of a hydrocarbyl material.

27. The process of claim 23, wherein said anode is selected from a group of precious metal anodic materials consisting of: Groups VIII and IB of the Periodic Table of The Elements, Aluminum, Tin, Zinc, Lead, Titanium, and Carbon as graphite or reticulated vitreous carbon (RVC).

28. The process of claim 27, wherein said anode is selected from a group consisting of: platinum, tin, gold, silver, or palladium.

\* \* \* \* \*